(12) United States Patent
DiMauro et al.

(10) Patent No.: US 7,367,961 B2
(45) Date of Patent: May 6, 2008

(54) INTRADISCAL INJECTION OF AUTOLOGOUS INTERFERON

(75) Inventors: Thomas M. DiMauro, Southboro, MA (US); Mohamed Attawia, Canton, MA (US)

(73) Assignee: Depuy Spine, Inc., Raynham, MA (US)

( * ) Notice: Subject to any disclaimer, the term of this patent is extended or adjusted under 35 U.S.C. 154(b) by 239 days.

(21) Appl. No.: 10/938,899

(22) Filed: Sep. 10, 2004

(65) Prior Publication Data

US 2006/0057128 A1    Mar. 16, 2006

(51) Int. Cl.
*A61M 37/00* (2006.01)
*A61M 5/00* (2006.01)

(52) U.S. Cl. ...................... 604/187; 604/6.08

(58) Field of Classification Search ............... 604/6.08, 604/20–22, 4.01, 240, 242, 241, 243, 181, 604/187, 199, 218; 128/897; 607/88, 90–94; 600/1–8; 606/1, 3, 13; 424/93.21; 514/44
See application file for complete search history.

(56) References Cited

U.S. PATENT DOCUMENTS

| | | | |
|---|---|---|---|
| 4,007,086 A | 2/1977 | Hamilton | |
| 4,168,261 A | 9/1979 | Edy | |
| 4,289,850 A | 9/1981 | Robinson | |
| 4,389,395 A | 6/1983 | Lerner et al. | |
| 4,426,323 A | 1/1984 | Jain | |
| 4,465,622 A | 8/1984 | Nobuhara et al. | |
| 4,485,032 A | 11/1984 | Olstowski et al. | |
| 4,485,038 A | 11/1984 | Chadha et al. | |
| 4,548,900 A | 10/1985 | Nobuhara et al. | |
| 4,680,261 A | 7/1987 | Nobuhara et al. | |
| 4,732,683 A | 3/1988 | Georgiades et al. | |
| 4,745,053 A | 5/1988 | Mitsuhashi | |
| 5,391,713 A | 2/1995 | Borg | |
| 6,159,188 A * | 12/2000 | Laibovitz et al. | 604/294 |
| 6,193,681 B1 * | 2/2001 | Davidner et al. | 604/6.08 |
| 6,582,993 B1 * | 6/2003 | Baba et al. | 438/118 |
| 2002/0032155 A1 | 3/2002 | Ferree | |
| 2002/0198599 A1 | 12/2002 | Haldimann | |
| 2003/0069639 A1 | 4/2003 | Sander | |
| 2003/0191356 A1 * | 10/2003 | Moreci | 600/4 |
| 2004/0127841 A1 * | 7/2004 | Briggs | 604/6.01 |

FOREIGN PATENT DOCUMENTS

| | | |
|---|---|---|
| RU | 2129011 C1 | 4/1999 |
| WO | 1999009051 A | 2/1999 |
| WO | 1999043271 A | 9/1999 |
| WO | 2003031566 A | 4/2003 |
| WO | 2003086280 A | 10/2003 |

* cited by examiner

Primary Examiner—Matthew F. DeSanto

(57) ABSTRACT

Administering to a patient Type I interferon or viable cells induced to produce Type I Interferon preferably into an inflamed joint, such an intervertebral disc, for example, is disclosed.

9 Claims, 2 Drawing Sheets

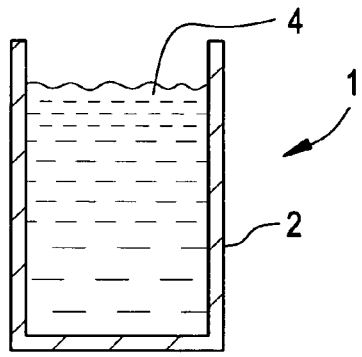
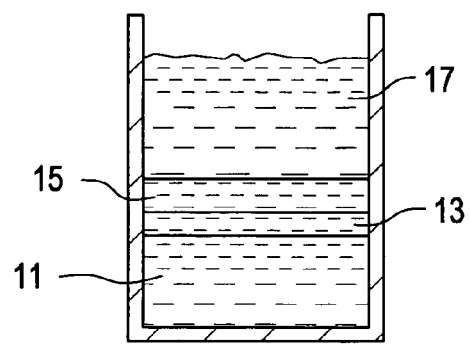
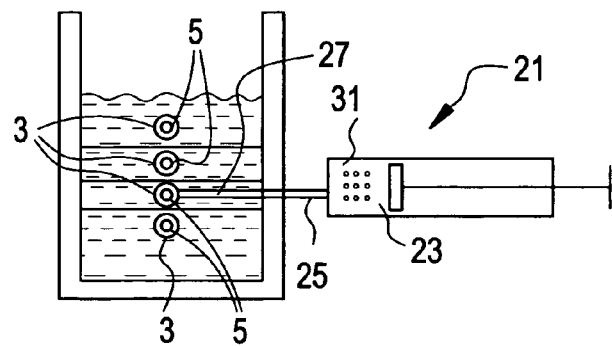
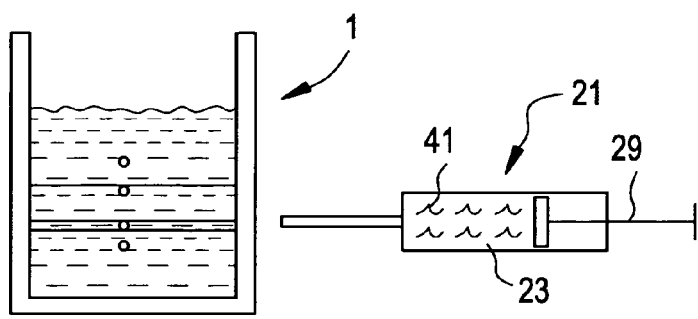
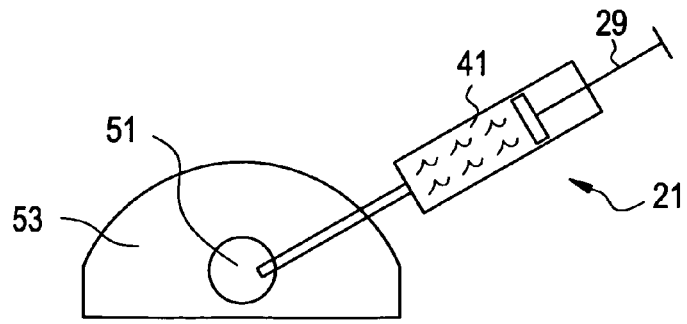

INTRADISCAL INJECTION OF AUTOLOGOUS INTERFERON

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines such as IL-1β and TNF-α as well as matrix metalloproteinases (MMPs). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells to emit larger than normal amounts of the above-mentioned cytokines. In other instances of DDD, genetic factors, such as programmed cell death, or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins.

As DDD progresses, the toxic levels of the cytokines present in the nucleus pulposus begin to degrade the extracellular matrix. In particular, the MMPs (under mediation by the cytokines) begin cleaving the water-retaining portions of the proteoglycans, thereby reducing their water-retaining capabilities. This degradation leads to a less flexible nucleus pulposus, and so changes the load pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

SUMMARY OF THE INVENTION

The present inventors have recognized the multiple benefits afforded by Type I interferon in treating DDD and so have developed a method of treating DDD comprising the step of providing an effective amount of Type I interferon into a degenerating disc.

In some embodiments, the Type I interferon is directly injected into the disc. Therefore, there is provided a method of treating degenerative disc disease in an intervertebral disc having a nucleus pulposus and an annulus fibrosus, comprising intradiscally administering an effective amount of a formulation comprising Type I interferon into an intervertebral disc. In some embodiments, the Type Interferon may be autologous, while in others it may be exogenous (such as recombinant interferon and/or allegeneic interferon).

In other embodiments, viable cells previously induced to produce Type I interferon are injected into the disc and thereafter produce an effective amount of interferon inside the disc. In particular embodiments, there is a method of treating inflammation wherein viable cells that have been induced to produce Type I interferon with an interferon-inducing agent are injected into a joint (preferably a degenerating disc), whereby the induced cells thereafter produce in vivo an effective amount of Type I interferon. This method is advantageous in that sufficient in vivo production of interferon is insured by the clinician's ability to provide as many viable cells as is needed. Moreover, since the induced cells are injected after induction, there is no need to wait for an ex vivo incubation period. Rather, the induction procedure takes only about one hour.

Therefore, in accordance with the present invention, there is provided a method of administering interferon to a patient, comprising:
  a) obtaining from the patient cells viable capable of producing interferon;
  b) mixing an interferon-inducing composition with the viable cells for a period sufficient to produce induced cells, and
  c) administering the induced cells to a location in the patient, whereby the induced cells in vivo produce Type I interferon at the location.

In other embodiments, ex vivo induced, autologous Type I interferon is injected into the disc. In particular embodiments, there is a method of treating inflammation wherein viable cells are induced ex vivo by an inducing agent to produce Type I interferon and then an effective amount of Type I interferon is injected into a joint (preferably a degenerating disc). This method is advantageous in that sufficient the interferon may begin acting immediately after injection.

Therefore, in accordance with the present invention, there is provided a method of administering interferon to a patient, comprising:
  a. obtaining from the patient cells viable capable of producing interferon;
  b. ex vivo mixing an interferon-inducing composition with the viable cells for a period sufficient the cells to emit interferon, and
  c. administering an effective amount of Type I interferon to a location in the patient.

In preferred embodiments, the cells are delivered in a concentrated fibrin glue to provide sustained release of the interferon.

Therefore, in accordance with the present invention, there is provided a method of treating degenerative disc disease in an intervertebral disc having a nucleus pulposus and an annulus fibrosus, comprising intradiscally administering an effective amount of a formulation comprising a therapeutic compound and fibrin glue having a fibrinogen concentration of at least 10 mg/ml.

In some embodiments, the Type I interferon is selected to be interferon-β. It is believed that interferon-β is strongly anti-inflammatory. IFN-β exerts antiviral and anti-inflammatory properties and modulates repair mechanisms, T-cell activation, lympocyte migration and immune suppression (Sciacsa, infra).

Sciacca, *J. NeuroVirology*, (2000) 6, Suppl. 2, S33-37 examined the effect of IFN-β upon the induction of IRAP in 3 human cell lines. Sciacca reported that very low levels (1000-10000 U/ml) of INF-β were required to induce physiologically significant amounts of IRAP (up to 9 ng/ml) in as little as two hours. Sciacca further found that IRAP expression induced by INF-β was found to peak at about 8 hours but remained high at 24 hours after induction, and that the 1000 U/ml dose of IFN-β was as effective an inducer of IRAP as the 10,000 U/mi dose. Scaiacca concluded that IFN-β was "one of the most effective inducers of IRAP when compared to other potent stimuli. The induction of IRAP by IFN-β occurs at both the mRNA and protein levels; it is rapid, occurring after 2-4 hours of stimulation, conspicuous in amount, being comparable to those obtained with potent LPS stimulation, and being specific . . . ".

Van Holten, *Arthritis Research Ther.*, 6(3) 2004, pp. R239-R249, discloses that IFN-β has anti-inflammatory properties, as it downregulates the key pro-inflammatory cytokines IL-β and tumor necrosis factor (TNF-α), and enhances the key anti-inflammatory cytokines IL-10 and IL-1 receptor antagonist production by lympocytes. Van Holten particularly points out that IFN-β's ability to induce IL-10 is important because IL-10 may be a potent anti-inflammatory cytokine, achieving the effect through suppression of TNF-α, IL-6 and IL-1 production by activated macrophages.

Tak, *Rheumatology*, 1999, 38, 362-369 reports that IFN-β was a "well known safety profile".

Palmer, *Ann. Rheum. Dis.*, 2004; 63;43-49, examined the effect of IFN-β stimulation of IRAP in human articular chondrocytes and synovial fibroblsts, and suggests that there may be "possible benefits of delivering IFN-β by intra-articular injections or gene therapy."

Ossege, *J. Neuroimmunology*, 91, (1998), 73-81, reports that IFN-β reduces the secretion of pro-inflammatory cytokines interferon-gamma, TNF-α and IL-13 by activated peripheral blood monocytes, and induces IL-10 and IL-6 synthesis. Ossege further reported that IFN-β upregulates the sTNFR molecules that are reported to antagonize and inhibit the effects of TNF-α.

Importantly, Ossege, supra, further reports that IFN-β induces the expression of TGF-β1 mRNA in PBMCs. Similarly, Noronha, *Neurology* 43, 355, 1993, reported an elevated release of TGF-β-a by PBMCs stimulated with IFN-β-1b in culture.

Ossege further noted that according to the known anti-inflammatory and immunosuppressive potentials of TGF-β1, it can be supposed that TGF-β enhancement is possibly one mechanism by which IFN-β-1b mediates its positive effects in the treatment of Multiple Scerosis (MS) patients. The finding that IFN-β induces TGF-β is critically important for DDD treatment, as TGF-β1 is a growth factor known to induce extracellular matrix (ECM) synthesis in chondrocytes present in an intervertebral disc. For example, Alini, *Spine* 28(5):446-54 (2003), reported that growth factors such as TGF-β, bFGF, and IGF-1 helped a cell-seeded collagen-hyaluronan scaffold produce the ECM proteins required for regenerating a nucleus pulposus.

Therefore, it appears that IFN-β holds a special advantage as a therapeutic compound in treating DDD in that it not only is a potent anti-inflammatory molecule that can antagonize the two of the key pro-inflammatory lynchpins of DDD (TNF-α and IL-1), IFN-β also induces the production of the key TGF-β protein involved in extracellular matrix production of collagen and proteoglycans that is critical to the repair of a damaged intervertebral disc.

In some embodiments, the Type I interferon selected is interferon-α. It is believed that interferon-α is an immunomodulatory compound—that is, it returns the environment to a neutral inflammatory status. Because of this modulatory effect, some investigators believe interferon-α may be a useful therapeutic compound for treating osteoarthritis.

Tilg, *J. Immunology*, injected healthy human volunteers with a single dose of 5×10$^6$ Units IFN-α and found circulating IRAP levels to be about 4 ng/ml. Tilg also conducted in vitro studies and found that about interferon levels as low as 1000 U/ml of INF-α produced about 4 μg/ml of IRAP in cultured PBMCs. Tilg concluded that IRAP may contribute to the anti-inflammatory effects of IFN-α, and that IFN-α has a down regulating effect on the synthesis of proinflammatory cytokines.

Tilg, *Expert Opin. Biol. Ther.* (20040 4(4) 469-481, reports that there is increasing evidence that IFN-α suppresses pro-inflammatory cytokines and in some cases acts as an anti-inflammatory agent, and that several in vivo models support an anti-inflammatory role for IFN-α. However, Tilg further acknowledges that IFN-α may have side effects and several clinical reports suggest that IFN-α has pro-inflammatory effects in vivo.

Perhaps the most optimistic report on the anti-inflammatory effects of IFN-α was contributed by Wong, *J. Rheumatology*, 2003, 30:5, pp. 934-940. Wong reported that IFN-α treatment of synovial cells resulted in the expression of two key anti-inflammatory compounds, IRAP and sTNFR. Of note, these results were accomplished at low levels of INF-α (10$^4$ Units IFN-Con/ml and with a short induction time (14 hours). Wong further reports that IFN-α had no effect upon production of proinflammatory cytokines IL-1β, TNF-α and OPGL. Wong speculates that IFN-α treatment may raise the levels of IRAP and sTNFR expression to a threshold such that effective antagonism of IL-1 and TNF-α occurs. Wong concludes that IFN-α may effectively block both the inflammation and join destruction in arthritic joints and that its therapeutic potential will be explored.

Brassard, *J. Leukoc. Biol.*, 71:565-81, 2002, also suggests the immunotherapeutic possibilities for interferon-α and teaches that INF-α an innate cell-mediated response and then participates in the transition of the initial host innate response into an effective, modulated adaptive immune response.

DESCRIPTION OF THE FIGURES

FIG. 2 is a cross-section of a centrifugation container filled with whole blood.

FIG. 3 is a cross-section of a centrifugation container filled with centrifuged blood.

FIG. 4 is a side view of a syringe filled with poly I:C having a needle inserted into the container of FIG. 3.

FIG. 5 is a side view of the syringe of FIG. 3 having a UV-producing unit attached thereto.

FIG. 6 is a cross-section of a syringe of the present invention injecting induced cells into the nucleus pulposus of an intervertebral disc.

DETAILED DESCRIPTION OF THE INVENTION

Figure 1:
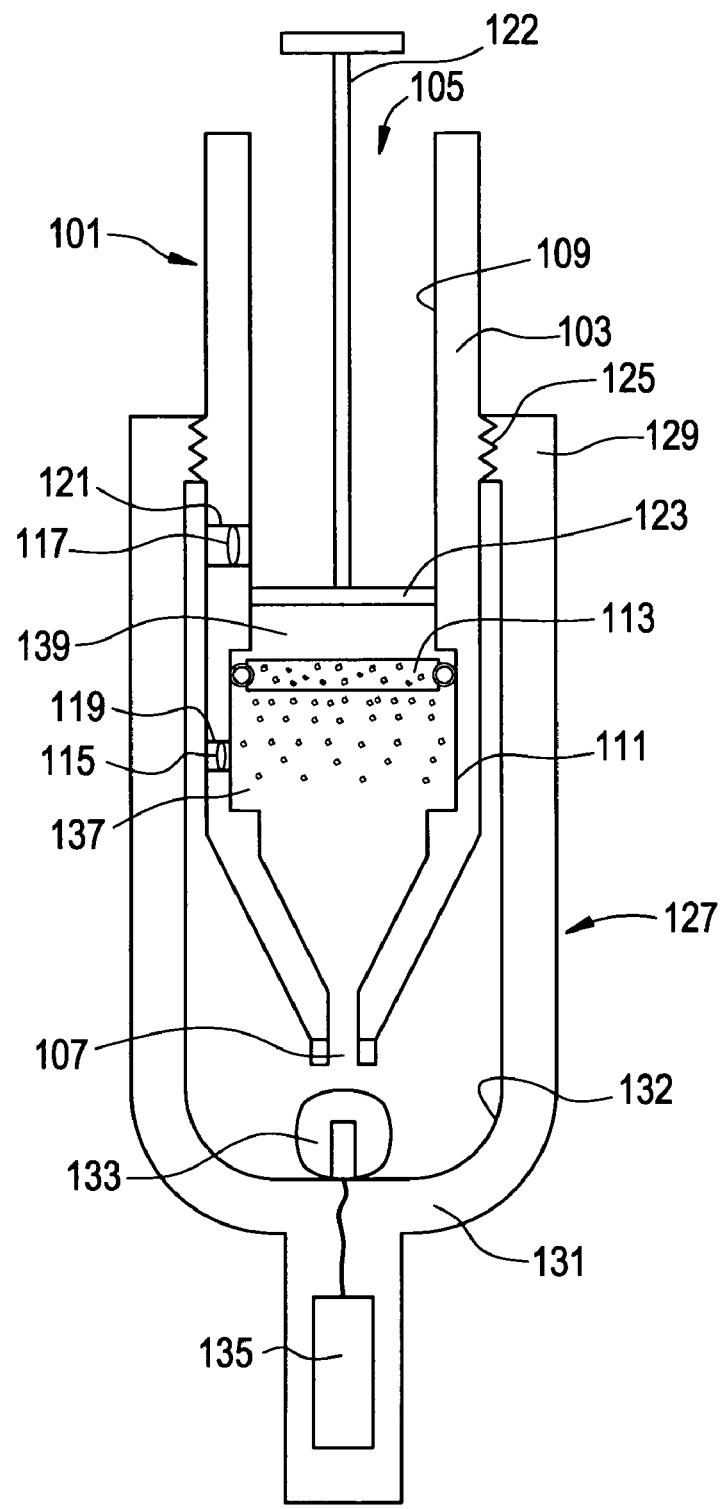
FIG. 1 is a cross-section of a syringe of the present invention having a UV-producing unit attached thereto.

For the purposes of the present invention, "Type I" interferon includes interferon-α, and interferon-β, but not interferon-gamma; "IRAP" refers to interleukin-1β receptor antagonist protein; "sTNFR" refers to soluble tumor necrosis factor receptor; "INF-α" refers to interferon-α or leukocyte-derived interferon; and "INF-β" refers to interferon-β or fibroblast-derived interferon.

Preferably, Interferon-α is produced by the induction of leukocytes. In preferred embodiments thereof, a physiologic fluid containing viable leucocyte cells is obtained from the patient. Preferably, the physiologic fluid is whole blood. Whole blood containing monocytes capable of producing interferon-α and is easily obtainable from the patient. More preferably, the whole blood is then fractionated by a conventional procedure (such as centrifugation or filtration) to obtain a selected portion of whole blood.

In some embodiments, the leucocytes are derived from the buffy coat fraction of whole blood. The buffy coat typically comprises about 5-10 vol % of whole blood Utilization of the buffy coat in the present invention is desirable because it contains a concentrated amount of monocytes capable of producing autologous interferon-α. Typically, the concentration of monocytes will be on the order of 10-20 fold over that found in whole blood. In some embodiments, a portion of the buffy coat may be used.

In other embodiments, the buffy coat is combined with other portions of blood in order to exploit desirable properties of molecules present in the other portions of blood. For example, in some embodiments, the buffy coat is combined with at least a portion of the plasma fraction. The plasma fraction contains fibrinogen and so may be useful for clotting the inducing composition to insure that the induced cells remain in the disc space, or for forming a sustained release device.

In other embodiments, the buffy coat is combined with thrombin in order to produce clotting.

In some embodiments, the buffy coat is combined with at least a portion of the platelet fraction of the blood. The platelet fraction contains growth factors such as TGF-β, which, upon release, can help stimulate extra cellular matrix production by natural disc cells.

Preferably, when the production of interferon-α is desired, leucocyte cells are selected as the viable cells of the present invention. Because these cells are easily obtained in a concentrated form from the simple centrifugation of a small amount of blood taken from the patient. More preferably, the monocyte fraction of white blood cells is selected as the viable cells of the present invention, as monocytes have been shown to produce interferon upon induction by poly I:C.

When the production of interferon-β is desired, the viable cells are typically fibroblasts. Suitable fibroblast may be obtained from a tissue selected from the group consisting of skin, muscle, and lung tissue. More preferably, skin tissue is selected as the source of fibroblasts.

In some embodiments, fibroblasts are conveniently obtained from the patient's tissue by first performing a biopsy upon the patient. In one example, a skin biopsy is performed using a biopsy punch and results in the removal of about a 5 mm×5 mm×5 mm portion of skin. This tissue sample is then subjected to collagen removal (by, for example, adding trypsin to the biopsy tissue) in order to free up the cellular components from the extracellular matrix. The cellular fraction is then subjected to centrifugation in order to concentrate the fibroblast fraction from other cellular components. The fibroblast isolation process of biopsy-collagen removal-centrifugation can generally take about 3-4 hours.

The inducer of viable cells are is selected from the group consisting of viral and non-viral agents. Typically, viral inducers are used to induce interferon-α, while non-viral inducers are used to induce interferon-β. However, non-viral inducers may also be used to induce interferon-α and viral agents may be used to induce interferon-β.

Preferred viral agents, include Sendai virus, Newcastle disease virus and influenza. However, the viral agent may be used in its active or inactive state. If the inactive state is desired, the viral agent may be treated with UV light.

Preferred non-viral inducers include molecules that mimic double strandard RNA molecules (dsRNA). One such molecule commonly used in interferon induction is polyriboinosinic-polyriboctyidylic acid ("poly I:C"). Other poly I:C-like molecules suitable for interferon induction include poly I:C complexed with poly-1-lysine and carboxymethylcellulose (poly I:C-LC"), which is more resistant to hydrolysis than poly I:C. In some embodiments, the low molecular weight poly I:C-LC molecules described in U.S. Pat. No. 4,389,395 ("Lerner") are used. In some embodiments, the dsRNA is heated, preferably to about 37-65° C. for about 30 minutes prior to induction. In some embodiments, about 100 mg/l of dsRNA is used.

In some embodiments using dsRNA, DEAE-Dextran is also added to the medium,as disclosed in U.S. Pat. No. 4,289,850, the specification of which is incorporated by reference in its entirety.

It has been reported that both interferon-α and interferon-β each upregulate both IRAP and sTNFR at concentrations of only about $10^3$ U interferon/ml. Of note, conventional crude interferon mixtures typically have an interferon concentration of about $10^4$-$10^5$ U/ml. For example, the US Patent literature reports the following concentrations of crude interferon:

| U.S. Pat. No. | Inventor | Interferon Conc. (U/ml) |
|---|---|---|
| 4,745,053 | Mitsuhashi | $2.7 \times 10^4$ |
| 4,485,038 | Chadha | $1-5 \times 10^4$ |

Therefore, the typical crude interferon mixture likely has a Type I interferon concentration sufficient to provide a therapeutic dose to an inflamed joint (especially the disc) without any time-consuming purification processing.

In a first method of producing interferon crude, an interferon-inducer (such as a dsRNA like poly I:C-LC) and autologous buffy coat are combined ex vivo and allowed to mix for about 2 hours. The mixing allows the inducer to enter the white blood cells. After two hours, the inducer in the medium is rinsed away. The induced cells are then injected into the disc. It is believed that this relatively simple process can be completed in less than 3 hours.

Once in the disc, the induced white blood cells will produce an autologous interferon within about 12 hours, and the induction will last for at least 48 hours. The autologous interferon will then interact with the white blood cells (and maybe disc cells) to produce TGF-β and antagonists of both IL-1β and TNF-α. These antagonists specifically and competitively bind to receptors of interleukin-1 and TNF-α, thereby slowing or stopping the inflammation associated with DDD, while the TGF-β will help synthesize proteoglycans that will repair the damaged disc.

Conventional interferon production technology includes a number of processes designed to enhance the production of interferon during the crude production step.

U.S. Pat. No. 4,007,086 ("Hamilton") discloses a method of enhancing interferon production comprising irradiating the interferon-producing cells with UV radiation after they have been mixed with the inducer. Hamilton reports a 10-fold increase in the interferon yield when the cells are irradiated for 20 twenty seconds after induction. Hamilton reports achieving interferon-$\beta$ levels of over $2\times10^4$ Units/ml (see tables 3 and 4 therein) in fibroblasts cells induced with poly I:C. Therefore, in some embodiments, the inducing agent-cell mixture is irradiated with an effective amount of UV radiation as taught in Hamilton, the specification of which is incorporated by reference in its entirety.

In some embodiments, a chemical adjunct capable of superinduction of the viable cells is used. In some embodiments, the superinducer is selected from the group consisting of ascorbic acid, an ascorbic acid derivative, and a vanadium compound. Such compounds are disclosed in U.S. Pat. No. 4,680,261, the specification of which is incorporated by reference in its entirety. In some embodiments, the superinducer is polyhydric alcohol, as disclosed in U.S. Pat. No. 4,548,900, the specification of which is incorporated by reference in its entirety. In others, the superinducer is a metabolic inhibitor such as cycloheximide and actinomycin, as disclosed by Vilcek, *Antimicrob. Ag. Chemother.* Vol.2, 1976, p. 476.

If desired, the production of interferon can be enhanced by priming. In a priming procedure, the viable cells are first exposed to a low level of interferon (such as 100 U/ml) for a suitable period (such as 6 hours) prior to their exposure to the inducer.

It has been reported in the literature that priming has the effect of increasing the rate of interferon production by about 10 fold. For example, Meager, *Infect. Immun.* August 1979, Vol. 25(2) pp. 658-663 reports that priming with 10-1000 U/ml in some cases results in a ten fold increase in interferon production.

Conventional interferon production technology further includes a number of unit processes designed to partially purify the concentration of interferon. Such conventional processes include the use of glass beads to capture the interferon; the use of a 10 kD filter to capture the interferon; the use of a molecular sieve to dewater the crude; the use of ammonium sulfate to precipitate out the interferon; and the use of ethanol extraction to precipitate out the interferon.

In general, the purification processes disclosed in U.S. Pat. No. 4,745,053 ("Matsuhashi"); U.S. Pat. No. 4,485,038 ("Chadha"); U.S. Pat. No. 4,732,683 ("Georgiades"); U.S. Pat. No. 4,168,261 ("Edy"); U.S. Pat. No. 4,465,622 ("Nobuhara"); U.S. Pat. No. 5,391,713 ("Borg"); U.S. Pat. No. 4,845,032 ("Obermeier") and U.S. Pat. No. 4,426,323 ("Jain"), the specifications of which are hereby incorporated by reference in their entireties, may be selected.

It is reasonable to expect that adoption of at least one of the partial purification techniques described above will lead to a 5-10 fold increase in the interferon concentration in the partially purified solution. For example, Chadra reports that sequential molecular filtration with 100K and 10K MW filters usually results in 5-10 fold purification of interferons; that hydrophobic chromatography results in a 10-15 fold purification, and that molecular sieving results in a 5-10 purification.

In some embodiments in which interferon is produced ex vivo, a one step purification of interferon-$\beta$ may be carried out using a monoclonal antibody. In one embodiment thereof, the monoclonal antibody procedure taught in Vonk, J. Interferon Res., 1983, 3(2), 169-75, the text of which is incorporated by reference in its entirety, is carried out to preferably obtain a 1000× purification.

It is believed that as little as $10^3$ UI interferon/ml is an effective immunosuppressive concentration. Wong, *J. Rheum.*, 30:5, 934, 2003, reported the upregulation of both IRAP and sTNFR in a culture containing $10^6$ monocytes/ml exposed to $10^4$ UI/ml of interferon-$\alpha$. Sciaca, supora, found as little as $10^3$ units/ml was physiologically effective in inducing IRAP in vitro.

Accordingly, in some embodiments of the present invention, the formulation comprises at least $10^3$ units interferon/ml, more preferably at least $10^4$ units interferon/ml, and more preferably at least $10^5$ units interferon/ml.

Preferably, the mixing container used to mix the inducer and viable cells is adapted to provide homogeneous mixing of the inducer and viable cells. In some embodiments, the container is a syringe. In other embodiments, the container is a column having a stopcock.

In some embodiments, the inducing agent is provided as a coating upon a substrate. The coating can be in either a solubilizable or an immobilized form. In some embodiments, the substrate can be an inner wall of a syringe or column. In others, the substrate may be in the forms of beads, such as glass or hydroxyapatite beads. In others, the substrate is organic and may be selected from agarose, hyaluronic acid and cellulose acetate.

Now referring to FIG. 1, there is provided a syringe 101 adapted for inducing and delivering viable cells of the present invention. This syringe is adapted to receive concentrated cells, dewater the cells, receive compounds such as the inducer and clotting agents, receive UV light, and finally deliver the induced cells to the patient.

The syringe comprises a barrel 103 having an inner wall 109, a proximal open end 105 and a distal open end 107. A recess 111 is provided in a portion of the inner wall in order to accommodate axial sliding of moveable filter 113. The syringe further has side ports 115 and 117 having gaskets 119 and 121 therein. The syringe further include a plunger 122 having a distal plug 123, and a threaded portion 125 adapted for threadable connection to a UV source.

The apparatus as shown further includes a UV source 127 adapted for connection to the syringe. The purpose of the UV source is to reliably produce an appropriate dose of UV radiation to the induced cells. The UV source has a threaded end 129 adapted for threadable connection with corresponding thread 125 on the outer surface of syringe 101. The UV source has a closed end 131 having an inner surface 132 having a cup shape which houses a UV light 133 connected to an energy source 135. The inner surface is preferably made of a reflective material to direct the UV light towards the induced cells, while cup shape of the inner surface also direct the UV light towards the induced cells In use, the clinician adds the concentrated cells (preferably, PBMCs) to the chamber 137 defined by the syringe barrel and filter. Next, the poly I:C inducer is added to the chamber, optionally through port 115. Next, the UV source is threaded onto the syringe and the UV source is activated to irradiated the cells with an effective amount of UV light. The clincian then waits up to two hours so that the inducer may induce the cells. After two hours, the inducing fluid is washed away, optionally by adding saline to the chamber through port 115. Next, plunger is partially withdraw from the barrel, thereby creating a vacuum and drawings fluid from the chamber 137 into space 139. A needle is then inserted into space 139 through port 117 in order to remove the withdrawn fluid.

Next, cryoprecipitate fibrinogen and thrombin are added to the chamber through port 115 in order to begin the clotting process.

Lastly, the plunger is advanced so that the contents of the chamber 137 are injected into the intervertebral disc.

Because, in some embodiments, the induced cells are immediately injected into the patient so that the patient serves as the incubation receptacle for the induced cells, there is no need to wait for ex vivo production of interferon. Accordingly, in preferred embodiment, the induced cells are injected into the disc less than 10 hours after the mixing step, more preferably less than 5 hours, more preferably less than three hours.

Upon administration into a joint space, the induced cells produce an in vivo interferon concentration of at least 103 Units interferon/cc, preferably at least 104 Units interferon/cc, more preferably at least 105 Units interferon/cc, more preferably at least 106 Units interferon/cc.

As the injection location is typically inflamed and has a local concentration of IL-1β, the interferon preferably produces an effective amount of IRAP to generate a local in vivo RAP: IL-1β ratio of at least 1000:1, more preferably at least 10,000:1 (as measured on a molar basis).

By way of comparison, Maeda taught that a level of about 50-100 ng IRAP/ml was needed to antagonize 1 mg IL-1/ml and to provide a therapeutic level of IRAP; Meijer reported that a minimum IRAP/IL-1 ratio of 10:1 is required to inhibit IL-1 activity; and Koch reported a disc producing a secretion rate of 4.29 ug IL-1β/$10^6$ cells/48 hr.

Preferably, the induced cells produced in the present invention are injected into an inflamed joint within the patient in a therapeutically effective amount. In some embodiments, the joint is a hip joint. In others, it is a knee joint. In others, it is an intervertebral disc. When the induced cells are injected into an intervertebral disc, they are either injected into the nucleus pulposus, the annulus fibrosus, or both, in order to treat low back pain. In other embodiments, the induced cells are injected epidurally near a nerve root in the vicinity of a ruptured intervertebral disc in order to treat sciatica.

In some embodiments, the interferon is produced in an amount effective to reduce or eliminate inflammation present within the local tissue. In others, the interferon is produced in an amount effective to act upon nerve endings present within the local tissue and thereby reduce or eliminate pain.

EXAMPLE I

This prophetic example describes a typical method of the present invention.

First, about 20 cc of blood is taken from the patient. Now referring to FIG. 2, the blood 4 is placed in a centrifugation container 1 adapted for centrifugation and having a side wall 2.

Now referring to FIG. 3, the blood is centrifuged to produce centrigued blood fractions including red blood cells 11, platelets 13, buffy coat 15 and platelet poor plasma 17.

Now referring to FIG. 4, a syringe 21 having a barrel 23 containing a poly I:C powder 31 and a needle 25 is provided. The centrifugation container has a plurality of side ports 3 having puncturable gaskets 5 therein. The clinician inserts the distal end 27 of the needle through the lowest gasket in the buffy coat portion of the fractionated blood.

Now referring to FIG. 5, the clinician pulls back upon the plunger 29. The vacuum created by withdrawl of the plunger causes the buffy coat fluid to enter barrel 23 of syringe 21, thereby reconstituting the poly I:C 31 and producing an poly I:C-rich buffy coat fluid 41.

Next, the clinician attaches the UV source and provides an effective amount of UV light to the cells as shown in FIG. 1.

After reconstitution of the poly I:C, the clinician then waits about 2 hours in order for the poly I:C to interact with and induced the monocytes in the fluid.

Next, the clinician uses a diagnostic test to verify that a particular disc within a patient has high levels of the particular interleukin-1β pro-inflammatory cytokine or TNF-α.

Next, still referring to FIG. 1, the physician partially withdraws the plunger 122 and dewaters monocyte the formulation.

Next, the clinician provides a local anesthetic (such as 5 ml lidocaine) to the region dorsal of the disc of concern to reduce subcutaneous pain.

Next, the clinician punctures the skin of the patient dorsal the disc of concern with a relatively large (e.g., 18-19 gauge) needle having a stylet therein, and advances the needle through subcutaneous fat and dorsal sacrolumbar ligament and muscles to the outer edge of the intervertebral disc.

Next, the stylet is removed from the needle.

Next, the clinician receives the syringe having the inducing composition of the present invention. This syringe has a smaller gauge needle adapted to fit within the larger gauge needle. This smaller needle is typically a 22 or 24 gauge needle. The barrel of the syringe contains the formulation of the present invention.

Next, the physician advances the smaller needle co-axially through the larger needle and past the distal end of the larger needle, thereby puncturing the annulus fibrosus. The smaller needle is then further advanced into the center of the nucleus pulposus. Finally, and now referring to FIG. 6, the clincian depresses the plunger 29 of the syringe 21, thereby injecting between about 0.5 and 1 ml of the formulation 41 comprising induced cells into the nucleus pulposus 51 of the intervertebral disc 53.

We claim:

1. An apparatus for the production and delivery of interferon-producing cells, comprising:
   a) a syringe having a barrel with an inner wall and an outer surface, a plunger disposed within the barrel and defining a chamber, wherein the chamber contains a buffy coat,
   b) a cap having an open end and an inner surface defining a closed end, wherein a portion of the inner surface of the cap is cup shaped and comprises a light reflective material,
   c) a UV light housed within the closed end of the cap, wherein the UV light induces cells within the chamber, and wherein the outer surface of the syringe is configured to be removably attached to the open end of the cap.

2. The apparatus of claim 1 wherein the buffy coat contains a concentrated amount of monocytes.

3. The apparatus of claim 2 wherein the concentration of monocytes is on the order of 10-20 fold over that found in whole blood.

4. The apparatus of claim 1 wherein the outer surface of the syringe has a threaded portion and the inner surface of the UV source has a mating threaded surface.

5. The apparatus of claim 1 wherein the cap further comprises an energy source in electrical connection with the UV light.

6. The apparatus of claim 1 wherein the UV light emits UV light in the range of less than 400 nm.

7. An apparatus for the production and delivery of interferon-producing cells, comprising:
   a) a syringe having a barrel with an inner wall and an outer surface, a plunger disposed within the barrel and defining a chamber, wherein the chamber contains cells, b) a cap having an open end and an inner surface defining a closed end, wherein a portion of the inner surface of the cap is cup shaped and comprises a light reflective material, c) a UV light housed within the closed end of the cap, wherein the UV light induces cells within the chamber, and wherein the outer surface of the syringe is configured to be removably attached to the open end of the cap.

8. An apparatus for the production and delivery of interferon-producing cells, comprising:

a) a syringe having a barrel with an inner wall and an outer surface, a plunger disposed within the barrel and defining a chamber, wherein the chamber contains an interferon-inducing agent housed within the chamber, b) a cap having an open end and an inner surface defining a closed end, wherein a portion of the inner surface of the cap is cup shaped and comprises a light reflective material, c) a UV light housed within the closed end of the cap, wherein the UV light induces cells within the chamber, and wherein the outer surface of the syringe is configured to be removably attached to the open end of the cap.

9. The apparatus of claim 8 wherein the interferon-inducing agent comprises polyriboinosinic-polyribocytidylic acid (poly I:C).

* * * * *